United States Patent

Fossati

Patent Number: 5,916,542
Date of Patent: Jun. 29, 1999

[54] NATURAL-BASE ANTISOLAR AND ANTIERYTHEMA MIXTURE

[76] Inventor: Antonio Fossati, Via Erba, 100, 20037, Paderno Dugnano, Italy

[21] Appl. No.: 08/658,480

[22] Filed: Jun. 5, 1996

[30] Foreign Application Priority Data

Jun. 9, 1995 [IT] Italy ................................. MI95A1236

[51] Int. Cl.⁶ .............................. A61K 7/42; A61K 7/44; A61K 7/00
[52] U.S. Cl. .............................. 424/59; 424/60; 424/400; 424/401
[58] Field of Search ................................ 424/59, 60, 400, 424/401

[56] References Cited

U.S. PATENT DOCUMENTS

| 5,100,918 | 3/1992 | Sunshine et al. | 514/557 |
| 5,538,740 | 7/1996 | Abad | 424/547 |
| 5,582,817 | 12/1996 | Otsa et al. | 424/59 |
| 5,674,912 | 10/1997 | Martin | 514/724 |

*Primary Examiner*—Shelley A. Dodson
*Attorney, Agent, or Firm*—Bucknam and Archer

[57] ABSTRACT

A natural-base antisolar and antierythema mixture comprises, in combination, aminoacids, vitamins and provitamins, glucides, lipides, nucleo-derivatives or other natural substances, either of an animal or vegetable nature, which, in set mixed amounts, are very efficient against the damage of ultraviolet rays.

8 Claims, No Drawings

NATURAL-BASE ANTISOLAR AND ANTIERYTHEMA MIXTURE

FIELD OF THE INVENTION

The present invention relates to a natural-base antisolar and antierythema mixture.

BACKGROUND OF THE PRIOR ART

As it is known, sunlight can seriously damage the skin.

Mainly the persons of clear skin and difficult browning are those most susceptible to damage deriving from an excessive exposure to the sun.

The ravaging effects, caused by an excessive radiation, are evident if one compares the conditions of the skin continuously exposed, for a long time, to the sun, such as for example the skin of the farmers, with the skin of persons having the same genetic characteristics, but not subjected to a continuous exposure.

Actually, in the case of a continuous exposure to the sun, and as the years pass, atrophy, deep wrinkles, telangiectasis, dryness of the skin and anomalous pigmentation occur.

The cutaneous ageing, even if it is not overcome, is much less evident and does not assume the gravity and intensity of the damage occurring in a person continuously exposed to the sun without any suitable protection.

The most evident signs of a premature and great cutaneous ageing can be detected just in those regions of the skin which are not usually protected by cloths, such as the face, neck, arms, hands and legs.

It is symptomatic, but explicative, the fact that a person thirty years old exposed during the day to the sun rays presents, in the not protected skin regions, the same damage of a person of fifty/sixty years.

On the contrary, that same person thirty years old, if remains in a closed environment, as it occurs in northern countries with northern climates, will have a skin like that of a twenty year old person.

The aggression to the skin due to the sunlight has been identified and acknowledged in the UV component, in particular at the wave length from 290 to 320 nanometers.

Also that portion of the UV rays from 320 to 400 nanometers causes to so-called actinic insults.

Moreover, the infrared rays, also called thermal rays since they transmit heat to the skin and exceed 700 nanometers, can overburden, together with the UV rays, the cutaneous damage occurring under a full sun exposure condition.

Actually, since the browning or tanning, or, better, melanin from which said browning derives, defends and protects the skin from the UV ray impact, an already tanned person should proceed with caution in taking the sun rays.

However, when the tanning is lacking, then sunlight must be taken, little by little, with a very great care and screening or shielding the skin by suitable and well calibrated solar filters is necessary.

In particular, it is absolutely necessary not to alternate sun periods with consequent tanning and no-sun periods with a tanning loss.

In fact, in this manner, the skin, not protected by melanin, would be exposed to continuous insults by UV rays.

This apparent paradox could bring a person to state that it would be better to take the sun continuously with the skin in a tanned condition instead of taking it alternatively "hiccup-wise".

Accordingly, it would be necessary to filter the sun rays in order to eliminate an excess of UV rays.

On the other hand, if a good tanning is desired, it is necessary that a portion of the UV rays reaches the skin in order to burst forth the formation of the required pigment.

However, with respect to the quality and amount of solar filters, it is practically not possible to adjust in a manner suitble for all types of skins requirements because of different delicacy, different doses and functionalities.

Because of the mentioned reason, and in order to prevent the skin from being seriously damaged, active agents or associations thereof should be used which, in addition to reducing the impact of the UV rays would be susceptible to preventing and repairing the negative effects of that part of radiation which, anyhow, must pass through the skin.

Accordingly, it will be necessary to use substances preventing the formation of and combating redness, inflammations and erythemas, which are due to free radicals, to a peroxidation as well as to the generation of substances which are damaging to the cells and tissues.

It is known that the skin is the most complex and extended organ of a human organism. Even if the human organism includes organs which are more important from a mere life standpoint, such as heart, brain, kidneys, lungs and so on, without which the life would be impossible, also the skin must be considered as essential for life. In this connection it is sufficient to think that a human organism cannot survive if a comparatively high amount of its skin surface is removed therefrom.

Those persons who do not expose themselves to the sun have a smooth skin, without stains up to ninety years, and present relaxation and only a deepening of the expression wrinkles.

On the contrary, those skins which have been excessively exposed to the insults of the sun will present dryness, deeper wrinkles, diffused naevus, an alternated color, couperoses, grooves, fissures, recesses and swellings. Moreover they have a hard rough and coriaceous undertouch.

All the above mentioned anomalous signs are indicative of great alterations and damage to the derma.

Actually, the skin is not only an organ for holding the other components of a body and for separating or defending them from the encompassing environment, but it is also the place of exchanges with the outer environment and for the synthesis of biochemical substances which, in addition to adjusting, coordinating and harmonizing their life, have an important meaning for the functionality and vital equilibrium of the overall organism.

Many histological variations have been disclosed because of the ageing of the skin under the effect of the sun rays and other causes damaging the skin.

At this time, it is necessary to distinguish the intrinsic causes which bring to the normal senescence from the extrinsic causes, in particular the sunlight, which bring to a premature much stronger cutaneous ageing.

The damages and faults caused by the UV rays can remain in a latent condition for tens of years but, at about fifty, as the defense mechanisms decrease and the normal regenerative processes lose efficiency, this damage becomes very evident.

In this connection it should be apparent that in addition to the aesthetic damage, degeneration and alteration of the cutaneous structure and functionality will also occur which cannot be recovered.

The premature ageing of the skin due to the sunrays will cause an alteration of the following structural, functional and biochemical parameters:

deep wrinkles;

an alteration of the color;

the appearance of sub-cutaneous small veins;

a modification of the thickness;

a dryness and roughness with a loss of the mechanical properties;

a loss of resiliency, with a degradation of the resilient fibers;

an alteration of the cell recovery and proliferation;

modification of the penetrability of the sebum secretion and circulation;

a degradation of the collagen and proteoglycans;

a formation of cross-linked bindings in bio-polymers;

anomalies in the immunological responses;

a cellular fall;

a cell and tissue disorganization;

keratosis;

insufficient recovery processes.

In view of all these negative effects exerted on the skin by the sunlight and, more specifically, by UV rays, this phenomenon cannot be ignored and it would not be possible to permit a devastation of the skin in favor of a striking and agreeable, temporary and transient tanning.

It is necessary to intervene before an irreversible end disaster and before a cutaneous ruin and to protect and cure the skin with attention, prudence, accuracy and, in other words, with intelligence.

This can be obtained by an accurate and exact use of preventive products.

At present the use of solar filters is greatly used by people exposing themselves for long time periods to the sunlight.

The use of solar filter containing creams and milks is suggested by an actual observation that the UV ray impact will cause on skins not naturally or artificially protected, an aggression with damage of various results (free radicals, peroxidation, erythemas, inflammation and so on).

This will cause the skin to prematurely age and, accordingly, on the face, the formation of the wrinkles which represent a visible minifestation of this UV damage.

At present it is necessary to prevent the violent UV (both UVA and UVB) impact from occurring, by using solar filters preventing the damaging radiation, in a different degree depending on the concentration, from penetrating through the skin with the consequent damage.

The commercially available solar filters are constituted by chemical synthetic substances, in general not physiological and not natural substances, which present the property of absorbing the UV rays thereby neutralizing their deleterious activity; however, they also have the consequent feature of hindering the tanning which, on the contrary, represents the continuously searched desire of a person exposing to the sun.

Anyhow, the most serious problem related to the use of conventional solar filters is the continuously increasing diffusion of cutaneous intolerances and reactions, due to the nature and concentration of these substances which will cause undesired side manifestations which, in some cases, discourage the use of said solar filters.

SUMMARY OF THE INVENTION

Accordingly, the object of the present invention is to solve the above mentioned problems by providing an antisolar mixture effective to absorb UV rays and having a remarkable antierythema activity as well as an anti-irritating activity.

Such a result would be very important since it would mean that, in the case in which the skin is affected by an excess of UV rays, the mixture is able to neutralize and eliminate the negative effects thereof.

In brief, the antisolar compositions of this invention are effective to absorb the damaging UV rays similar to the solar filters but without any side effects. Moreover they are surprisingly provided with a great antierythema and anti-irritating activity.

The first feature is a very important one and the second feature will provide the antisolar compositions with a unique advantage which is not exhibited by the conventional solar filters.

A main object of the present invention is to provide such an antisolar mixture which is effective to prevent erythemas and irritations from occurring, thereby allowing an easier and more complete or intensive tanning in a shorter time, without disagreeable secondary effects and without negative consequences for the skin as time elapses, such as fading, wrinkles and premature senescence.

Another object of the present invention is to provide such an antisolar mixture which can be used for making solar creams, antisolar oils and as an anti-aging and anti-wrinkle active agent, in the form of a facial cream so as to also protect from a temporary exposure to the sun, while preventing and combating the cutaneous irritations and reactions and all the skin senescence processes.

According to one aspect of the present invention, the above mentioned objects, as well as yet other objects, which will become more apparent hereinafter, are achieved by an antisolar screening and antierythema mixture of a natural base type characterized in that said mixture comprises, in combination, aminoacids, vitamins, provitamins, nucleoderivatives and polymers thereof, UV absorbing vegetable extracts or other innocuous natural substances, of either animal or vegetable origin, effective against the UV ray damage.

By way of example, it is possible to mention, among the amino acids: tryptophan, histidine, phenylalanine tyrosine; tyrosine; among the vitamins and provitamins: B6, A, E, several tocopherols, betacarotene, bioflavonoids, ubidecarenone; among said nucleo derivatives: nucleosides, nucleotides and polymers thereof, uric acid; among the vegetable extracts, in all of the commercial preparations: carrots, bilberry, aloe, cascara, frangula, camomile, hyperic, calendula, elicrise, licorice.

It is also possible to use other substances of natural origin, and having an anti-UV effect, such as for example, gammaorizanole and others.

All of these substances and extracts, as suitably mixed, even partially, will provide the desired results.

Further features and advantages of the invention will become more apparent from the following detailed disclosure of the antisolar screening and antierythema natural base mixture, which is substantially prepared by mixing vitamin B6, in a rate of 5–15%, vitamin A, in a rate of 0.5–1.5%, vitamin E or a tocopherol mixture, in a rate of 3–7%, betacarotene, in a rate of 0.1–0.5%, unidecarenone, in a rate of 0.5–2%, tryptophan, in a rate of 2–6%, histidine in a rate of 1–3%, phenylalanine, in a rate of 1–3%, tyrosine, in a rate of 1–3%, bioflavonoids, in a rate of 5–15%, uric acid in a rate of 1–2%, nucleosides or nucleotides, in a rate of 3–7%, gamma orizanole, in a rate of 3–7%, dry carrot extract in a rate of 0.5–2%, dry aloe extract, in a rate of 0.5–2%, the remaining part being constituted by solvent and diluent substances such as glycerine, propylenglycol in a 1:1 ratio.

The above mixture will allow to replace the prior art chemical synthetic products by natural products having a surprisingly analogous solar filtering and antierythema efficiency of fully natural products, assuring a very satisfactory local tolerability.

Hereinbelow is shown a practical Example for making 100 g of the antisolar mixture, according to an optimal formulation:

Vitamin B6—10 g

Vitamin A—1 g

Vitamin E or tocopherol mixture —5 g

Betacarotene —0.1 g

Ubidecarenone —1 g

Tryptophan —4 g

Histidine —2 g

Phenylalanine —2 g

Tyrosine —2 g

Bioflavonoids —10 g

Uric acid —1.5 g

Nucleosides or nucleotides and/or polymers thereof —5

Gamma orizanole —5 g

Dry carrot extract —1 g

Dry aloe extract —1 g

Solvent and diluent

Glycerine-propylenglycol 1:1 g.b. to 100 g.

The mixture has the great advantage that it can be used in addition to solar products, also in conventional antiaging, anti-wrinkles, protective creams, for people who are daily exposed to the solar light, in those periods in which, without remaining for a long time under the sun for tanning, they carry out normal activities requiring period, even of short duration, of exposure to the light.

Thus, the skin will be protected and defended against any damages deriving from the sunlight, such as: premature ageing, wrinkles, dryness, loss of tone and elasticity, anomalous thickenings, roughness, and so on.

In order to provide a low protection solar cream, the mixture is used in a rate of 3% with a self emulsifying base; to provide a mean protection the solar cream is used with an amount of 6% of the mixture with an auto-emulsifying base and, for providing a high protection the solar cream is used preferably with a rate of 12% of the mixture, together with an autoemulsifying base.

If it is desired to increase the anti-UV power of the mixture without using very high doses and with skins which cannot absolutely support the UV rays, then it is possible to add to the end product reflecting powders, such as titanium oxide, zinc oxide, mica and other UV reflecting powders which, being insoluble and accordingly, not absorbable, will not cause cutaneous irritations or sensibilizations, contrary to the conventional chemically synthetized solar filters.

The antisolar mixture, as suitable formulated, can be prepared either by emulsion or it can also be carried out in any other suitable composition for cutaneous use, such as oils, lotions, sprays and the like.

For preparing an antiaging, antiwrinkles, protective formulation the antisolar mixture will be associated with placenta, collagen, soluble elastic and/or other antiageing substances having a well experimented antiaging activity, mixed with carrier, emulsifying and preserving agents.

The precious anti-irritating action of the natural filters, applied after the impact of the UV rays on a not protected skin, can be explained by the anti-radical and anti-oxidative action of the mixture according to the present invention.

The solar filtering and antierythema action of the mixture has not been found in any of the prior solar filters and mixtures thereof.

As stated, the precious anti-irritating effect of the antisolar mixture can be explained by the antiradical and antioxidative action of the mixture.

It is known that the solar erythema can be attributed to the formation of free radicals and lipoperoxides which are very damaging for the cells, and which derive from the impact of the UV on the skin.

The invention, as disclosed, is susceptible to several modifications and variations and moreover all of the details can be replaced by other technically equivalent elements.

I claim:

1. An antisolar screening and antierythema mixture, made of natural substances either of animal or vegetable origin, efficient against damaging UV rays, said mixture comprising aminoacids, vitamins or provitamins, nucleoderivatives, and vegetable extracts, wherein said aminoacids comprise tryptophan, histidine, phenylalanine, tyrosine, said vitamins and provitamins comprise vitamin B6, vitamin A, vitamin E, tocopherols, betacarotene, bioflavonoids, ubidecarenone, said nucleoderivatives comprise nucleosides, nucleotides and polymers thereof, uric acid, and said vegetable extracts comprise carrots, bilberry, aloe, cascara, frangula, camomile, hyperic, calendula, elicriso, licorice.

2. The mixture, according to claim 1, which comprises vitamin B6, vitamin A, vitamin E or tocopherols, betacarotene, ubidecarenone, tryptophan, histidine, phenylalanine, tyrosine, bioflavonoids, uric acid, nucleosides or nucleotides, gamma orizanole, dry carrot extract, dry aloe extract, and glycerinepropylenglycole as a solvent.

3. The mixture according to claim 2, which comprise vitamin B6 in a rate of 5–15% by weight, vitamin A in a rate of 0.5–1.5% by weight, vitamin E or a mixture of tocopherols in a rate of 3–7% by weight, said betacarotene in a rate of 0.1–0.5% by weight, tryptophan in a rate of 2–6% by weight, histidine in a rate of 1–3% by weight, phenylalanine in a rate of 1–3% by weight, tyrosine in a rate of 1–3% by weight, bioflavonoids in a rate of 5–15% by weight, uric acid in a rate of 1–2% by weight, nucleosides uric acid in a rate of 1–2% by weight, nucleosides or nucleotides in a rate of 3–7% by weight, gamma orizanole in a rate of 3–7% by weight, dry carrot extract in a rate of 0.5–2% by weight, dry aloe extract in a rate of 0.5–2% by weight, the remaining part of said mixture comprising a glycerine-propylenglycol solvent and diluent in a 1:1 ratio.

4. The mixture, according to claim 3, wherein vitamin B-6 is present in a rate of 10%, vitamin A in a rate of 1%, vitamin E or mixture of tocopherols in a rate of 5%, betacarotene in a rate of 0.1%, unidecarenone in a rate of 1%, tryptophan in a rate of 4%, histidine in a rate of 2%, phenylalanine in a rate of 2%, tyrosine in a rate of 2%, bioflavonoids in a rate of 10%, uric acid in a rate of 1.5%, nucleosides or nucleotides in a rate of 5%, gamma orizanole in a rate of 5%, dry carrot extract in a rate of 1%, dry aloe extract in a rate of 1%.

5. The mixture according to claim 4 which comprises 10 g of vitamin B6, 1 g of vitamin A, 5 g of vitamin E or tocopherols, 0.1 g of betacarotene, 1 g of ubidecarenone, 4 g of tryptophan, 2 g of histidine, 2 g of phenylalanine, 2 g of tyrosine, 10 g of bioflavonoids, 1.5 g of uric acid, 5 g of a member selected from the group consisting of nucleosides, nucleotides and mixtures thereof, 5 g gamma orizanole, 1 g of dry carrot extract, 1 g of dry aloe extract, glycerine-propylene glycol as a solvent in the ratio of 1:1 to a total of 100 g.

6. A solar emulsion including said mixture according to claim 1, wherein said solar emulsion comprises 3% for a low protection, 6% for a middle protection and 12% for a high protection of said mixture, mixed with an auto-emulsifying base.

7. An antisolar composition including said mixture according to claim 1, wherein said antisolar composition comprises, 3% for a low protection, 6% for a middle protection and 12% for a high protection of said antisolar mixture, mixed with cosmetic lyposolvents.

8. An anti-aging, anti-wrinkle, and protective cream, comprising a mixture according to claim 1, wherein said cream comprises, in a carrier, emulsifier and preserving agent mixture, 3% of said antisolar mixture, 2% of placenta, 1% of collagen and 2% of soluble elastin.

\* \* \* \* \*